(12) United States Patent
Allen et al.

(10) Patent No.: US 8,100,130 B2
(45) Date of Patent: Jan. 24, 2012

(54) MEDICAL DRAPE

(75) Inventors: Fred L. Allen, Wonder Lake, IL (US); Francis A. Czajka, Libertyville, IL (US); Eric G. Holcomb, Cincinnati, OH (US)

(73) Assignee: Medline Industries, Inc., Mundelein, IL (US)

( * ) Notice: Subject to any disclaimer, the term of this patent is extended or adjusted under 35 U.S.C. 154(b) by 378 days.

(21) Appl. No.: 11/594,630

(22) Filed: Nov. 8, 2006

(65) Prior Publication Data
US 2007/0113859 A1 May 24, 2007

Related U.S. Application Data

(60) Provisional application No. 60/734,399, filed on Nov. 8, 2005.

(51) Int. Cl.
*A61B 19/08* (2006.01)
*A61B 19/00* (2006.01)

(52) U.S. Cl. .................................. 128/853; 128/849

(58) Field of Classification Search .................. 128/853, 128/854, 849, 850, 851, 852, 855, 856
See application file for complete search history.

(56) References Cited

U.S. PATENT DOCUMENTS

| | | | |
|---|---|---|---|
| 3,750,664 A | 8/1973 | Collins | |
| 3,799,161 A * | 3/1974 | Collins | 128/854 |
| 3,826,253 A * | 7/1974 | Larsh et al. | 128/854 |
| 3,881,474 A | 5/1975 | Krzewinski | |
| 3,956,048 A | 5/1976 | Nordgren | |
| 4,027,665 A * | 6/1977 | Scrivens | 128/854 |
| 4,041,942 A | 8/1977 | Dougan et al. | |
| 4,134,398 A | 1/1979 | Scrivens | |
| 4,323,062 A | 4/1982 | Canty | |
| 4,334,529 A | 6/1982 | Wirth | |
| 4,471,769 A * | 9/1984 | Lockhart | 128/849 |
| 4,479,492 A * | 10/1984 | Singer | 128/853 |
| 4,489,720 A | 12/1984 | Morris et al. | |
| 4,553,538 A | 11/1985 | Rafelson | |
| 4,569,341 A | 2/1986 | Morris | |
| 4,596,245 A | 6/1986 | Morris | |
| 4,616,642 A | 10/1986 | Martin et al. | |
| 4,664,103 A | 5/1987 | Martin et al. | |
| 4,869,271 A | 9/1989 | Idris | |
| 5,106,362 A * | 4/1992 | Gilman | 602/47 |
| 5,140,996 A * | 8/1992 | Sommers et al. | 128/849 |
| 5,454,381 A * | 10/1995 | DeHart | 128/849 |
| 5,611,356 A | 3/1997 | Rothrum | |
| 5,765,566 A * | 6/1998 | Rothrum | 128/849 |
| 5,975,082 A | 11/1999 | Dowdy | |
| 6,298,855 B1 * | 10/2001 | Baird | 128/849 |
| 6,694,981 B2 | 2/2004 | Gingles et al. | |
| 6,843,252 B2 * | 1/2005 | Harrison et al. | 128/849 |
| 2003/0188753 A1 * | 10/2003 | Jascomb | 128/853 |
| 2006/0076024 A1 * | 4/2006 | Duarte | 128/849 |

* cited by examiner

*Primary Examiner* — Patricia Bianco
*Assistant Examiner* — Ophelia Hawthorne
(74) *Attorney, Agent, or Firm* — Nixon Peabody LLP

(57) ABSTRACT

A medical drape is disclosed. The drape comprises a main portion having a front side, a back side, a first edge, a second edge, a top, and a bottom. The first and second edges are positioned opposite one another. The top and the bottom are positioned opposite one other. The drape further comprises a first and a second fenestration extending completely through the main portion and spaced generally equidistant from a vertical axis. The vertical axis is generally parallel to the first and second edges. The drape further comprises a third and a fourth fenestration extending completely through the main portion and are spaced generally equidistant from the vertical axis. The first and second fenestrations are closer to the top than the third and fourth fenestrations.

18 Claims, 4 Drawing Sheets

# MEDICAL DRAPE

CROSS-REFERENCE TO RELATED APPLICATION

This application claims the benefit of U.S. Provisional Application No. 60/734,399, filed Nov. 8, 2005, which is hereby incorporated by reference in its entirety.

FIELD OF THE INVENTION

This invention relates to medical drapes, and more specifically to a medical drape used in connection with surgical or medical procedures, the drape being reversible and having multiple, removably covered access sites.

BACKGROUND OF THE INVENTION

Medical drapes are widely used during the performance of surgical and other medical procedures as a protective measure. Medical drapes may be used to cover a patient during surgical or other medical procedures. Medical drapes are made sterile and are intended to prevent the possibility of infection being transmitted to the patient. Medical drapes provide protection to the patient by creating a sterile environment surrounding the surgical site and maintaining an effective barrier that minimizes the passage of microorganisms between non-sterile and sterile areas. To perform adequately, the drape should be made of a material that is resistant to blood, plasma, serums, and/or other bodily fluids to prohibit such fluids from contaminating the sterile field.

Medical drapes may, for example, be manufactured for use in connection with catheters such as central venous catheters (CVCs). CVCs may be used, for example, for intravenous drug therapy and/or parenteral nutrition. If the catheter or area surrounding the catheter becomes contaminated during or after being inserted into a patient, complications such as catheter site infection, suppurative phlebitis, and/or septicemia may result.

To minimize the risk of infection associated with catheterization, medical drapes often include fenestrations, or apertures, that extend completely through the drape to provide access to an adjacent area of the patient's body (for example, the subclavian area, the brachial area, or the femoral area) over which the respective fenestration lies. Because of the open nature of the fenestrations, a catheter may be inserted through the fenestration(s) and into the area of the patient's body adjacent to the fenestration(s).

Existing medical drapes that include fenestrations have several disadvantages. For example, if a medical drape includes more than one fenestration, not all of which are being used for inserting a catheter, the area of the patient's body adjacent the unused fenestration(s) remains unnecessarily exposed during the procedure. Thus, bodily fluids and/or other surgical fluids that may contain microorganisms may contact the exposed area of the patient's body through the unused fenestration(s) and possibly lead to infection.

Moreover, existing medical drapes having fenestrations only provide access to one area (for example, the subclavian area) of the body. Thus, more than one drape may be required for procedures that require a catheter to be inserted into multiple areas of the patient's body (for example, the subclavian area and the brachial area). Utilizing multiple drapes during one procedure is both inconvenient for health care providers and dangerous for patients because it exposes the patient to potential contamination, which may lead to infection.

Thus, it would be desirable to have a medical drape that assists in addressing one or more of the above disadvantages.

SUMMARY OF THE INVENTION

According to one embodiment, a medical drape is disclosed. The drape comprises a main portion having a front side, a back side, a first edge, a second edge, a top, and a bottom. The first and second edges are positioned opposite one another. The top and the bottom are positioned opposite one another. The drape further comprises a first fenestration and a second fenestration extending completely through the main portion. The first and second fenestrations are spaced generally equidistant from a vertical axis. The vertical axis is generally parallel to the first and second edges. The drape further comprises a third fenestration and a fourth fenestration extending completely through the main portion. The third and fourth fenestrations are spaced generally equidistant from the vertical axis. The first and second fenestrations are closer to the top than the third and fourth fenestrations.

According to another embodiment, a medical drape is disclosed. The drape comprises a main portion having a front side, a back side, a first edge, a second edge, a top, and a bottom. The first and second edge are positioned opposite one another. The top and bottom are positioned opposite one other. The drape further comprises a first side portion coupled to a first edge of the main portion. The drape further comprises a second side portion coupled to a second edge of the main portion. The drape further comprises a first fenestration and a second fenestration extending completely through the main portion. The first and second fenestrations are spaced generally equidistant from a vertical axis. The vertical axis is generally parallel to the first and second edges. The drape further comprises a third fenestration and a fourth fenestration extending completely through the main portion. The third and fourth fenestrations are spaced generally equidistant from the vertical axis. The drape further comprises at least one peel patch removably coupled to the front side of the main portion. The at least one peel patch is positioned over at least one of the first, second, third, and fourth fenestrations. The first and second fenestrations are closer to the top than the third and fourth fenestrations.

According to one process of the present invention, a method of making a medical drape is disclosed. The method comprises the act of providing a main portion having a front side, a back side, a first edge, a second edge, a top, and a bottom. The first and second edges are positioned opposite one another. The top and the bottom are positioned opposite one another. The method further comprises the act of forming a first fenestration extending completely through the main portion. The method further comprises the act of forming a second fenestration extending completely through the main portion. The second fenestration is spaced generally the same distance from a vertical axis and the top as the first fenestration. The vertical axis is generally parallel to the first and second edges. The method further comprises the act of forming a third fenestration extending completely through the main portion. The third fenestration is positioned farther from the top than the first and second fenestrations. The method further comprises the act of forming a fourth fenestration extending completely through the main portion. The fourth fenestration is spaced generally the same distance from the vertical axis and the top as the third fenestration.

The above summary of the present invention is not intended to represent each embodiment or every aspect of the present invention. The detailed description and Figures will describe many of the embodiments and aspects of the present invention.

BRIEF DESCRIPTION OF DRAWINGS

The foregoing and other advantages of the invention will become apparent upon reading the following detailed description and upon reference to the drawings.

Figure 1:
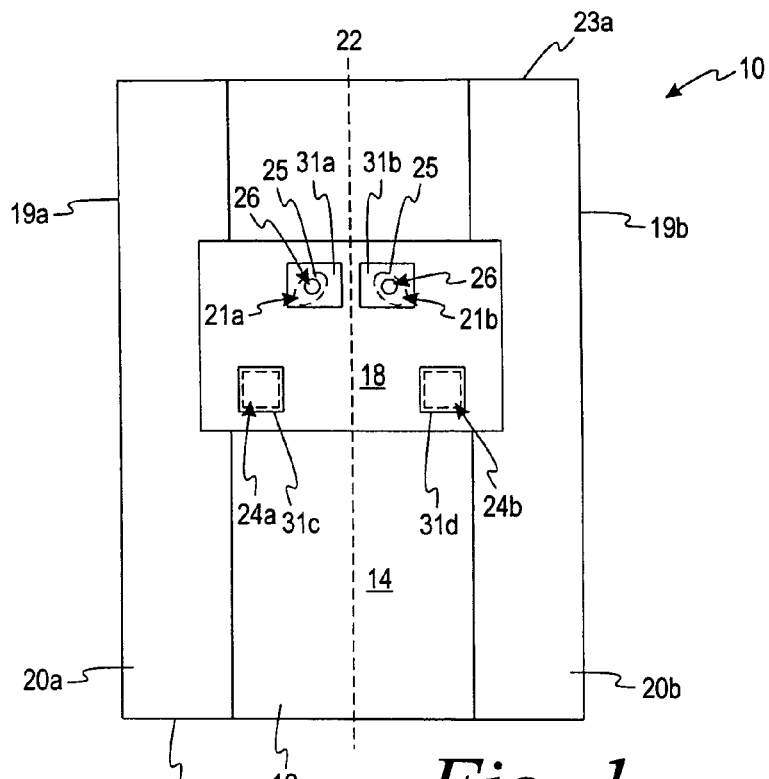
FIG. 1 is a plan view of a front side of a medical drape according to one embodiment.

While the invention is susceptible to various modifications and alternative forms, specific embodiments are shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF THE PREFERRED EMBODIMENTS

Figure 2:
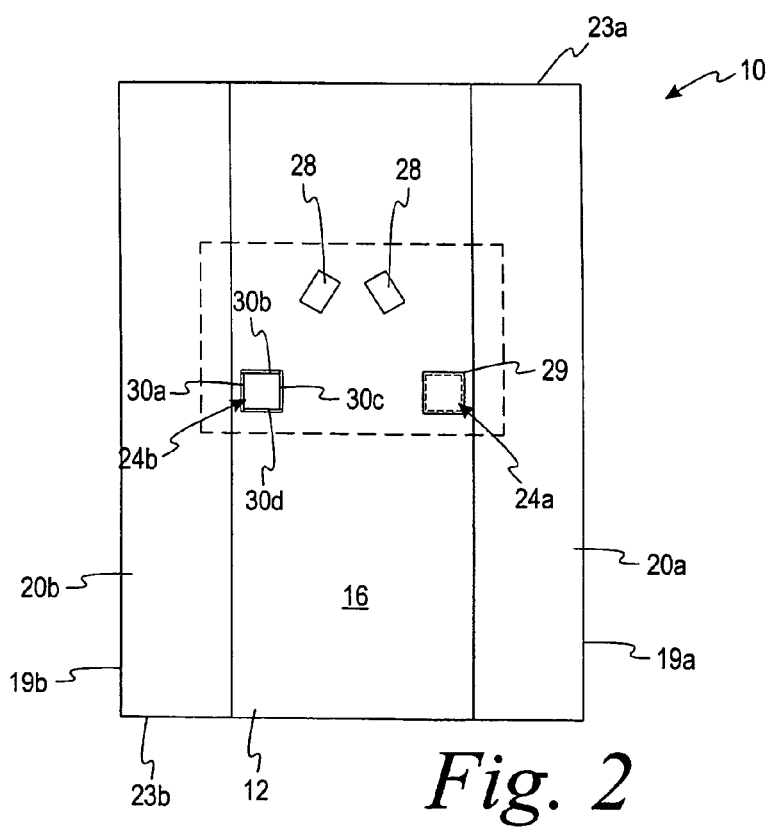
FIG. 2 is a plan view of a back (patient's) side of the medical drape of FIG. 1.

FIG. 1 shows a front side of a medical drape 10 according to one embodiment as it would appear after being unfolded and ready for use in a surgical or medical procedure (for example, catheterization, angiography, and radiology). A back (i.e., patient's) side of the medical drape 10 is shown in FIG. 2. It may be desirable that the drape 10 have dimensions suitable for covering the patient's entire body, including, in some embodiments, the patient's head and face to assist in maintaining the sterility of the surgical area and thereby lower the risk of infection. In such embodiments, the total length of the drape 10 generally ranges from about 115 in. to about 125 in. (about 292 cm to about 318 cm). In other embodiments, the drape 10 may cover less than the patient's entire body and may have a length ranging generally from about 30 in. to about 50 in. (about 76 cm to about 127 cm). The total width of the drape 10 generally ranges from about 75 in. to about 80 in. (about 190 cm to about 204 cm).

The drape 10 generally comprises a main portion 12 having a front side 14, which faces away from a patient when in use (see FIG. 1), and a back side 16, which contacts the patient when in use (see FIG. 2). The main portion 12 further includes a top area 23a, a bottom area 23b, and side edges 19a, 19b. The main portion 12 is generally made of a water-repellent or water-impermeable material and/or is coated with such a water-repellent or water impermeable material to prevent the passage of bodily fluids and/or contaminating microorganisms. For example, the main portion 12 may be made of various woven, non-woven, and/or hydroentangled materials. The base fabrics used in the main portion 12 may include Airlaid, spunlace and blends of polyester, polypropylene, and polyethylene.

The drape 10 further comprises a reinforcement portion 18 coupled to the front side 14 of the main portion 12. The reinforcement portion 18 is positioned generally equidistant from each side edge 19a, 19b of the main portion 12. The reinforcement portion 18 may be made from, for example, a non-woven material including, but not limited to, polypropylene, airlaid, and wood pulp. The material used in the reinforcement portion 18 is generally capable of absorbing from about 300 to about 500 percent of its own weight in fluids. Thus, the reinforcement portion 18 assists in minimizing the risk of cross-contamination by absorbing any blood or other fluid produced at or near the surgical site either directly from the patient, from irrigation fluids used to flush the site, or the like. It may be desirable that the material used in the reinforcement portion 18 be durable and/or tear resistant. It may also be desirable that the material used in the reinforcement portion 18 have a 4-5 rating on the Martindale Abrasion Test (ASTM D4966). The weight of the material used in the reinforcement portion 18 is generally greater than that of the main portion 12. The reinforcement portion 18 may be attached to the main portion 12 by any suitable means including, but not limited to, adhesives, thermal bonding, ultrasonic bonding, tape, or combinations thereof. The length of the reinforcement portion 18 may range from about 30 in. to about 35 in. (about 76 cm to about 89 cm). The width of the reinforcement portion 18 may range from about 45 in. to about 55 in. (about 114 cm to about 140 cm).

The drape 10 may also include a first side portion 20a and a second side portion 20b. The first and second side portions 20a, 20b may, for example, be made of an embossed polyethylene film or another suitable material(s) that is generally less expensive than the material used in the main portion 12. Thus, the first and second side portions 20a, 20b may provide a cost-effective mechanism to provide a greater width to the drape 10 to enhance the area of coverage of the drape 10. The first and second side portions 20a, 20b may be coupled to the main portion 12 by any suitable means including, but not limited to, adhesives, thermal bonding, ultrasonic bonding, tape, or combinations thereof. The length of each of the first and second side portions 20a, 20b may range from about 115 in. to about 125 in. (about 292 cm to about 318 cm). The width of each of the first and second side portions 20a, 20b may range from about 15 in. to about 20 in. (about 38 cm to about 51 cm).

Figure 3A:
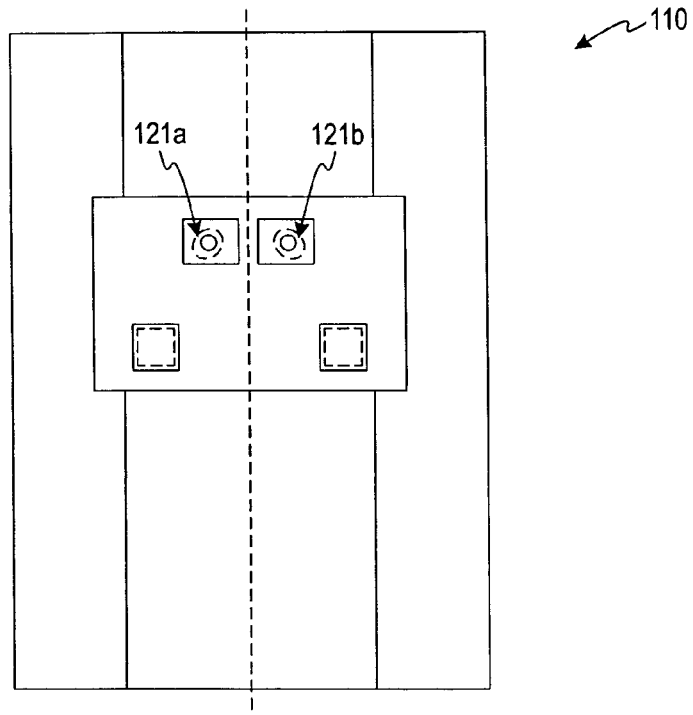
FIGS. 3a-3c are plan views of front sides of medical drapes according to other embodiments.
Figure 3B:
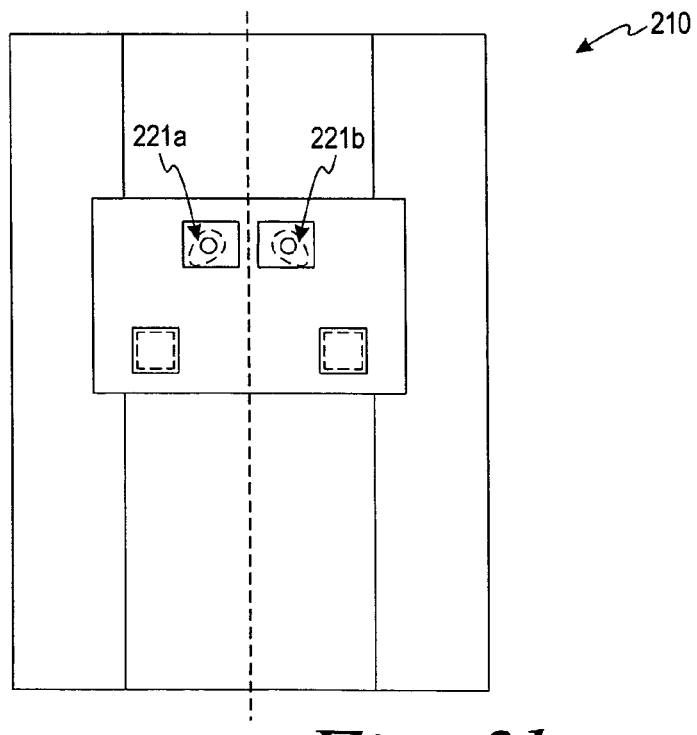
Figure 3C:
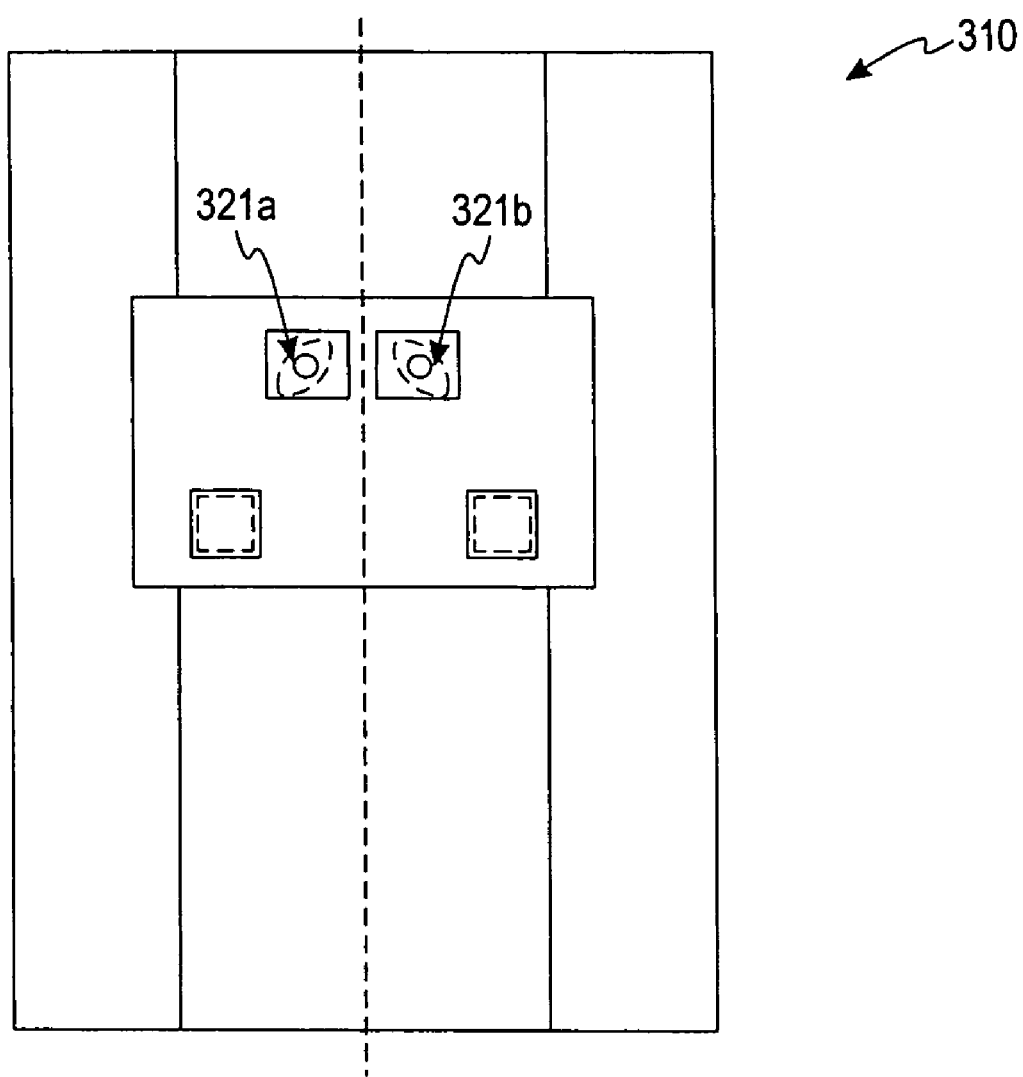

Positioned on and extending completely through the main portion 12 and the reinforcement portion 18 are a first fenestration 21a and a second fenestration 21b. The first and second fenestrations 21a, 21b allow for a surgical or other medical procedure to be performed therethrough. In the embodiment of FIG. 1, the first and second fenestrations 21a, 21b are generally egg-shaped. In addition to the use of generally egg-shaped fenestrations(s), the first and second fenestrations may be generally oval-shaped, pear-shaped, football-shaped, or the like. For example, the embodiment of FIG. 3a depicts a drape 110 having a first fenestration 121a and a second fenestration 121b that are generally oval-shaped. The embodiment of FIG. 3b depicts a drape 210 having a first fenestration 221a and a second fenestration 221b that are generally pear-shaped. The embodiment of FIG. 3c depicts a drape 310 having a first fenestration 321a and a second fenestration 321b that are generally football-shaped. It is contemplated that the first and second fenestrations may have shapes other than those shown in the illustrated examples in FIGS. 1, 3a, 3b, and 3c. It is further contemplated that the drape may have any of the properties described herein, regardless of the shape and/or location of the fenestrations.

It may be desirable for the first and second fenestrations 21a, 21b to be contoured to the general shape of the area of the body to which they are adjacent. For example, the first and second fenestrations 21a, 21b of FIG. 1 are angled with respect to one another such that the tops of the first and second fenestrations 21a, 21b are closer to a vertical axis 22 (which may be imaginary) than the bottoms of the first and second fenestrations 21a, 21b so that the first and second fenestrations 21a, 21b are contoured to the general shape of the subclavian area. Each of the first and second fenestrations 21a, 21b may have an area ranging from about 5 in² to about 55 in² (about 32 cm² to about 355 cm²). In some embodiments, the first and second fenestrations 21a, 21b may have an area ranging from about 5 in² to about 10 in² (about 32 cm² to about 65 cm²). The first and second fenestrations 21a, 21b are positioned generally equidistant from the vertical axis 22 running generally through the center of the drape 10 and generally parallel to the side edges 19a, 19b. The first and second fenestrations 21a, 21b should be positioned so that there is a sufficient amount of space between them to minimize potential tearing between the first and second fenestrations 21a, 21b. Moreover, the space between the first and second fenestrations 21a, 21b should be sufficient to cover, for example, the sternum and ribcage for subclavian catheterization. The distance between each of the first and second fenestrations 21a, 21b and the vertical axis 22 may range from about 1 in. to about 6 in. (about 2 cm to about 16 cm).

According to some embodiments, the first and second fenestrations 21a, 21b are positioned so that when the top area 23a of the drape 10 is placed over a patient's head, the first and second fenestrations 21a, 21b are positioned over the patient's subclavian area. When the drape 10 is, for example, opened "upside down" so that the top area 23a is placed over the patient's feet, the first and second fenestrations 21a, 21b are positioned generally over the patient's femoral artery. Thus, the drape 10 may be used in multiple procedures, including, for example, subclavian catheterization and/or femoral catheterization.

The drape 10 of the embodiments described herein further includes a third fenestration 24a and a fourth fenestration 24b positioned on and extending completely through the main portion 12 and the reinforcement portion 18. Although the third and fourth fenestrations 24a, 24b of FIGS. 1 and 2 are generally square-shaped, it is contemplated that other general shapes including, but not limited to, rectangles, other polygons, circles, and ovals may be used. The third and fourth fenestrations 24a, 24b may have an area ranging from about 5 in² to about 55 in² (about 32 cm² to about 355 cm²). In some embodiments, the third and fourth fenestrations 24a, 24b may have an area ranging from about 5 in² to about 10 in² (about 32 cm² to about 65 cm²). The size and shape of the third and fourth fenestrations 24a, 24b of the illustrated embodiments are generally large enough that brachial access to several veins including the antecubital fossa, the basilic vein, the cephalic vein, and the median cubital vein may be achieved.

The third and fourth fenestrations 24a, 24b may be used for PICC (peripherally inserted central catheter) line insertion. A PICC line may be inserted through the third or fourth fenestration 24a, 24b into one of the large veins in the arm (e.g., the antecubital fossa), usually near the bend of the elbow. The PICC line can be used for taking blood for blood tests, giving chemotherapy drugs, giving blood transfusions, or the like.

The third and fourth fenestrations 24a, 24b are positioned generally equidistant from the vertical axis 22. The third and fourth fenestrations 24a, 24b are generally positioned a sufficient distance from the vertical axis 22 such that there is a sufficient amount of space between the third and fourth fenestrations 24a, 24b to cover, for example, the patient's torso and/or abdominal region during brachial catheterization. The distance between each of the third and fourth fenestrations 24a, 24b and the vertical axis 22 may range from about 5 in. to about 15 in. (about 12 cm to about 39 cm). Because the third and fourth fenestrations 24a, 24b in the embodiment of FIGS. 1 and 2 are generally used for access to the veins of the arm, the third and fourth fenestrations 24a, 24b are positioned generally further from the vertical axis 22 than the first and second fenestrations 21a, 21b. Although the drape 10 of the illustrated embodiment includes four fenestrations 21a, 21b, 24a, 24b (i.e., two pairs of fenestrations), it is contemplated that a different number of fenestrations may be used including, for example, three, five, or six. The number of fenestrations used may depend on a variety of factors such as the type of surgical or other medical procedures for which the drape may be used or the like.

Figure 4:
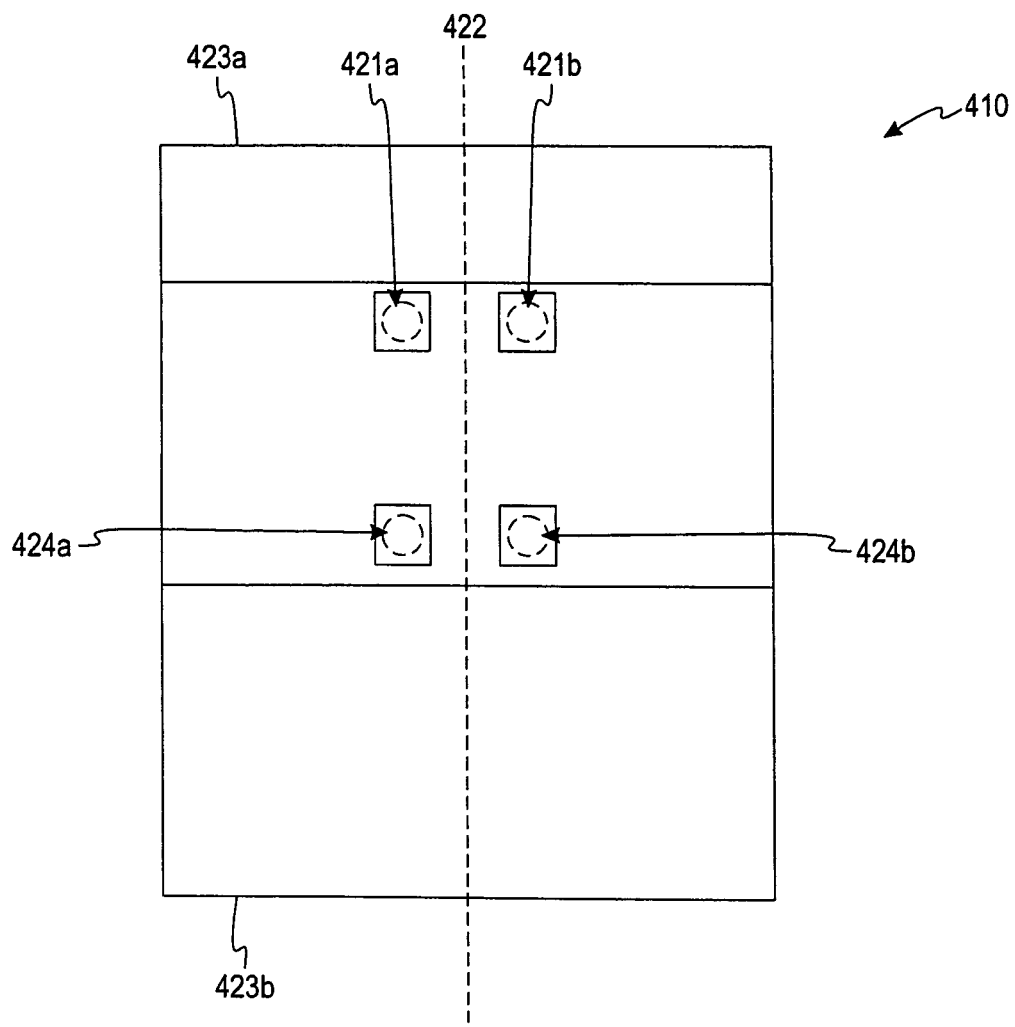
FIG. 4 is a plan view of a front side of a medical drape according to yet another embodiment.

Referring now to the embodiment of FIG. 4, a front side of a medical drape 410 according to another embodiment is illustrated. The drape 410 of FIG. 4 is generally similar in structure and characteristics to the drapes 10, 110, 210, 310 of FIGS. 1-3c described above. For example, the drape 410 includes a first fenestration 421a and second fenestration 421b positioned near a top area 423a of the drape 410. The drape 410 further includes a third fenestration 424a and a fourth fenestration 424b positioned closer to a bottom area 423b of the drape 410. The fenestrations 421a, 421b, 424a, 424b extend completely through the drape 410. In the embodiment of FIG. 4, however, the third and fourth fenestrations 424a, 424b are positioned generally the same distance away from a vertical axis 422 as the first and second fenestrations 421a, 421b. Although in the embodiment of FIG. 4, the fenestrations 421a, 421b, 424a, 424b are generally round in shape, any suitable shape may be used. It is contemplated that the fenestrations 421a, 421b, 424a, 424b may have a generally similar structure and/or characteristics as those described above.

The multiple fenestrations (e.g., fenestrations 21a, 21b, 24a, 24b of FIG. 1) are desirable because they provide the health care professional with multiple access sites through which a catheter or catheters may be inserted. Thus, the drape (e.g., drape 10 of FIG. 1) may be used for procedures requiring subclavian catheterization, brachial catheterization, femoral catheterization, or combinations thereof.

The fenestrations may be covered with an adhesive incise film. It is contemplated that none, one, or more of the fenestrations may include the incise film. In the illustrated embodiment of FIG. 1, the first and second fenestrations 21a, 21b include an incise film 25. The composition of the incise film 25 is well known to those skilled in the art of medical drapes. One example of an incise film that may be used is OpSite® Incise film manufactured by Smith & Nephew, Inc. (Memphis, Tenn.). The incise film 25 may be generally transparent so that the health care provider may have clear visibility for locating the correct position for inserting the catheter(s). The incise film 25 may be positioned on top of the reinforcement portion 18, between the reinforcement portion 18 and the main portion 12, or on the back side 16 of the main portion 12, so long as an exposed adhesive side of the incise film 25 faces toward the patient. The incise film 25 includes an access port 26 being positioned on and extending completely through the incise film 25. The access port 26 allows a catheter(s) to be readily inserted without any cutting, puncturing, or further modification of the drape 10 or incise film 25. Although the access port 26 of the illustrated embodiment is circular, it is contemplated that other general shapes including, but not limited to, rectangles, other polygons, circles, and ovals may be used. The access port 26 may have an area ranging from about 3 in² to about 5 in² (about 19 cm² to about 33 cm²). It is contemplated that the drapes 110, 210, 310, and 410 of FIGS. 3a-4 may also include adhesive incise film generally similar in structure and characteristics to the incise film 25 described with respect to FIG. 1.

The exposed adhesive side of each incise film 25 employed in FIG. 1 is covered by at least one release liner 28 (see FIG.

2), which is located on the back side 16 of the main portion 12. The release liner may be one continuous piece of liner, strips, or the like. When the release liner 28 is removed, the adhesive side of the incise film 25 may be coupled to the patient to keep the drape 10 and, in particular, the first and second fenestrations 21a, 21b, in place during the procedure.

Alternatively or additionally, adhesive may be applied to an area surrounding any such fenestrations on the back side 16 of the drape 10 so that such fenestrations remain in place during the surgical or medical procedure. The adhesive area may then be covered by one or more release liners and/or release liner strips. Referring to FIG. 2, for example, an adhesive surrounding the third fenestration 24a is covered by one release liner 29 which overlies the entire third fenestration 24a. In embodiments where a release liner(s) is used, it is contemplated that the release liner(s) may overlie the entire fenestration(s) or a portion of the fenestration(s). In an alternative embodiment shown in FIG. 2, the fourth fenestration 24b includes a separate release liner strip 30a, 30b, 30c, 30d coupled to each side of the fourth fenestration 24b to cover the exposed adhesive. Thus, the release liner strips 30a, 30b, 30c, 30d do not overlie the entire fourth fenestration 24b. In embodiments where release liner strips are used, it is contemplated that the release liner strips may overlie a portion of the fenestration(s) or none of the fenestration(s). This may be desirable in some embodiments so that a health care professional's view through the fenestration is not obstructed. Although the illustrated embodiment of FIGS. 1 and 2 shows the first and second fenestrations 21a, 21b having incise film 25 and release liners 28, a third fenestration 24a having a release liner 29, and a fourth fenestration 24b having release liner strips 30a, 30b, 30c, 30d, it is contemplated that any combination of incise film(s), release liner(s), and/or release liner strip(s) may be used in any of the drapes described herein. It is also contemplated that none, one, or more of the fenestrations in the various embodiments of the drapes described herein may include respective release liner(s) and/or release liner strip(s). In other embodiments, the drape includes neither incise films nor adhesive surrounding the fenestrations on the back side 16 of the drape 10.

The drape may further include one or more peel patches, which may be positioned over one or more of the fenestrations on the front side of the drape. In the embodiment of FIG. 2, for example, outer edges of peel patches 31a, 31b, 31c, 31d may include, for example, adhesive, for coupling each of the peel patches 31a, 31b, 31c, 31d to the drape 10. Although not necessary, it may be desirable for the peel patches 31a, 31b, 31c, 31d to be transparent or generally transparent so that a health care professional's view through the fenestrations 21a, 21b, 24a, 24b is not obstructed. The peel patches 31a, 31b, 31c, 31d may also be made of a non-transparent material. The peel patches 31a, 31b, 31c, 31d may be removed to expose the fenestrations 21a, 21b, 24a, 24b and/or the incise films 25 and the access ports 26 so that a health care provider may insert a catheter(s) therethrough. The peel patches 31a, 31b, 31c, 31d cover the unused fenestrations until needed, thereby providing a mechanism for maintaining a sterile environment surrounding the fenestrations 21a, 21b, 24a, 24b when the fenestrations 21a, 21b, 24a, 24b are not in use. For example, a patient's body may include markings indicating where a catheter should be inserted, over which the fenestrations 21a, 21b, 24a, 24b and, thus, the peel patches 31a, 31b, 31c, 31d are positioned. The peel patches 31a, 31b, 31c, 31d are particularly useful in surgical or medical procedures in which less than all of the fenestrations 21a, 21b, 24a, 24b are used. It is contemplated that none, one, or more of the fenestrations of any of the drapes described herein may include peel patches. It is further contemplated that other mechanisms suitable for removably covering the fenestrations may be used.

According to one embodiment, the front side 14 of the drape 10 includes a slick surface surrounding one or more of the fenestrations. Referring to FIGS. 1 and 2, for example, the slick surface may be formed by positioning a single-side tape around the fenestrations 21a, 21b, 24a, 24b such that an adhesive side of the single-side tape contacts the reinforcement portion 18 and a slick side of the single-side tape is exposed. In use, the outer edges of the peel patches 31a, 31b, 31c, 31d having adhesive or other suitable attachment means thereon may overlie the slick surface(s). Thus, when a peel patch 31a, 31b, 31c, 31d is removed, the reinforcement portion 18 of the drape is less likely to become damaged and/or torn. It is contemplated that the slick surface may be formed on any of the drapes described herein.

According to another embodiment, the adhesive of the peel patches 31a, 31b, 31c, 31d is adapted to remain substantially on the peel patch 31a, 31b, 31c, 31d after the peel patch 31a, 31b, 31c, 31d has been removed. Thus, only a negligible amount, if any, of adhesive remains on the drape 10 and/or the slick surface surrounding the fenestration 21a, 21b, 24a, 24b after the peel patch 31a, 31b, 31c, 31d has been removed. This may be desirable so that the adhesive of the peel patch 31a, 31b, 31c, 31d does not interfere with a catheter(s) inserted through the fenestration 21a, 21b, 24a, 24b and/or with the surgical or other medical procedure generally. This embodiment may be applied to any of the drapes described herein.

In use, the drape 10 may be unfolded such that the top area 23 of the drape 10 is placed over a patient's head. In the embodiments depicted in FIGS. 1 and 2, one or more of the release liners 28, 29 and/or the release liner strips 30a, 30b, 30c, 30d are removed, and the incise film 25 and/or adhesive may be coupled to the patient so that each of the first and second fenestrations 21a, 21b may be placed over the subclavian area and each of the third and fourth fenestrations 24a, 24b may be placed over the veins of the arm. The desired peel patch 31a, 31b, 31c, 31d may be removed so that a catheter(s) may be inserted, for example, into the right central vein, the left central vein (through the access ports 26 for subclavian insertion), the right antecubital fossa, and/or the left antecubital fossa (through the third and fourth fenestrations 24a, 24b for brachial insertion). Alternatively, the drape 10 may be positioned over the patient such that the top area 23 of the drape 10 is placed over a patient's foot area such that a catheter(s) may be inserted into the femoral artery through one or both of the first and second fenestrations 21a, 21b. The drapes of FIGS. 2-4 may be similarly used.

According to alternative embodiment A, a medical drape comprises a main portion having a front side, a back side, a first edge, a second edge, a top, and a bottom, the first and second edges being positioned opposite one another, the top and the bottom being positioned opposite one other, a reinforcement portion coupled to the front side of the main portion, a first fenestration and a second fenestration extending completely through the main portion and the reinforcement portion, the first and second fenestrations being spaced generally equidistant from a vertical axis, the vertical axis being generally parallel to the first and second edges, and a third fenestration and a fourth fenestration extending completely through the main portion and the reinforcement portion, the third and fourth fenestrations being spaced generally equidistant from the vertical axis, wherein the first and second fenestrations are closer to the top than the third and fourth fenestrations, and wherein the third and fourth fenestrations are positioned a greater distance from the vertical axis than the first and second fenestrations.

According to alternative embodiment B, the drape of alternative embodiment A, wherein the main portion is made of a water-repellent or water-impermeable material.

According to alternative embodiment C, the drape of alternative embodiment A, wherein the reinforcement portion is made of a non-woven material.

According to alternative embodiment D, the drape of alternative embodiment A, wherein the reinforcement portion is coupled to the main portion by adhesive, thermal bonding, ultrasonic bonding, tape, or a combination thereof.

According to alternative embodiment E, the drape of alternative embodiment A, wherein the reinforcement portion has a length of between about 30 inches and about 35 inches and a width of between about 45 inches and about 55 inches.

According to alternative embodiment F, the drape of alternative embodiment A further comprises a first side portion coupled to the first edge of the main portion and a second side portion coupled to the second edge of the main portion, wherein the first and second side portions are made of a polymeric film.

According to alternative embodiment G, the drape of alternative embodiment F, wherein the first and second side portions are coupled to the main portion by adhesive, thermal bonding, ultrasonic bonding, tape, or a combination thereof.

According to alternative embodiment H, the drape of alternative embodiment F, wherein the first and second side portions have a width of between about 15 inches and about 20 inches.

According to alternative embodiment I, the drape of alternative embodiment A, wherein the first and second fenestrations are generally egg-shaped.

According to alternative embodiment J, the drape of alternative embodiment A further comprises at least one incise film positioned over at least one of the first, second, third, and fourth fenestrations, the incise film including an adhesive side, the incise film including an access port extending completely therethrough, and at least one release liner positioned on the back side of the drape, wherein the at least one release liner covers the adhesive side of a corresponding at least one incise film.

According to alternative embodiment K, the drape of alternative embodiment A, wherein the back side of the drape further includes adhesive positioned around at least a portion of at least one of the first, second, third, and fourth fenestrations, the adhesive being covered with at least one release liner.

According to alternative embodiment L, the drape of alternative embodiment A further comprises at least one peel patch removably coupled over at least one of the first, second, third, and fourth fenestrations, the at least one peel patch being removably coupled to the front side of the main portion.

According to alternative embodiment M, the drape of alternative embodiment L, wherein outer edges of the at least one peel patch include adhesive, the at least one peel patch being removably coupled to the main portion via the adhesive outer edges.

According to alternative embodiment N, the drape of alternative embodiment M further comprises at least one slick surface surrounding at least one of the first, second, third, and fourth fenestrations on the front side of the drape, wherein the outer adhesive edges of the at least one peel patch are adapted to overlie a corresponding at least one slick surface.

According to alternative embodiment O, the drape of alternative embodiment M, wherein the adhesive is adapted to remain substantially on the at least one peel patch upon removal of the at least one peel patch.

According to alternative embodiment P, the drape of alternative embodiment A, wherein the first and second fenestrations are adapted to be placed over a patient's subclavian area, and wherein the third and fourth fenestrations are adapted to be placed over the patient's brachial area.

According to alternative embodiment Q, the drape of alternative embodiment P, wherein the first and second fenestrations are further adapted to be placed over a patient's femoral area via the first and second fenestrations.

According to alternative embodiment R, the drape of alternative embodiment A, wherein the drape has a length of between about 115 inches and about 125 inches and a width of between about 75 inches and about 80 inches.

According to alternative embodiment S, the drape of alternative embodiment A further comprises one or more additional fenestrations.

According to alternative embodiment T, a medical drape comprises a main portion having a front side, a back side, a first edge, a second edge, a top, and a bottom, the first and second edge being positioned opposite one another, the top and bottom being positioned opposite one other, a reinforcement portion coupled to the front side of the main portion, a first side portion coupled to a first edge of the main portion, a second side portion coupled to a second edge of the main portion, a first fenestration and a second fenestration extending completely through the main portion and the reinforcement portion, the first and second fenestrations being spaced generally equidistant from a vertical axis, the vertical axis being generally parallel to the first and second edges, a third fenestration and a fourth fenestration extending completely through the main portion and the reinforcement portion, the third and fourth fenestrations being spaced generally equidistant from the vertical axis, and at least one peel patch removably coupled to the front side of the main portion, the at least one peel patch being positioned over at least one of the first, second, third, and fourth fenestrations, wherein the first and second fenestrations are closer to the top than the third and fourth fenestrations, and wherein the third and fourth fenestrations are positioned a greater distance from the vertical axis than the first and second fenestrations.

According to alternative embodiment U, the drape of alternative embodiment T, wherein the main portion is made of a water-repellent or water-impermeable material.

According to alternative embodiment V, the drape of alternative embodiment T, wherein the reinforcement portion is made of a non-woven material.

According to alternative embodiment W, the drape of alternative embodiment T, wherein the reinforcement portion is coupled to the main portion by adhesive, thermal bonding, ultrasonic bonding, tape, or a combination thereof.

According to alternative embodiment X, the drape of alternative embodiment T, wherein the reinforcement portion has a length of between about 30 inches and about 35 inches and a width of between about 45 inches and about 55 inches.

According to alternative embodiment Y, the drape of alternative embodiment T, wherein the first and second side portions are made of a polymeric film.

According to alternative embodiment Z, the drape of alternative embodiment T, wherein the first and second side portions are coupled to the main portion by adhesive, thermal bonding, ultrasonic bonding, tape, or a combination thereof.

According to alternative embodiment AA, the drape of alternative embodiment T, wherein the first and second side portions have a width of between about 15 inches and about 20 inches.

According to alternative embodiment AB, the drape of alternative embodiment T, wherein the first and second fenestrations are generally egg-shaped.

According to alternative embodiment AC, the drape of alternative embodiment T further comprises at least one incise film positioned over at least one of the first, second, third, and fourth fenestrations, the incise film including an adhesive side, the incise film including an access port extending completely therethrough, and at least one release liner positioned on the back side of the drape, wherein the at least one release liner covers the adhesive side of a corresponding at least one incise film.

According to alternative embodiment AD, the drape of alternative embodiment T, wherein the back side of the drape further includes adhesive positioned around at least a portion of at least one of the first, second, third, and fourth fenestrations, the adhesive being covered with at least one release liner.

According to alternative embodiment AE, the drape of alternative embodiment T, wherein outer edges of the at least one peel patch include adhesive, the at least one peel patch being removably coupled to the main portion via the adhesive outer edges.

According to alternative embodiment AF, the drape of alternative embodiment AE further comprises at least one slick surface surrounding a corresponding at least one of the first, second, third, and fourth fenestrations on the front side of the drape, wherein the outer adhesive edges of the at least one peel patch are adapted to overlie a corresponding at least one slick surface.

According to alternative embodiment AG, the drape of alternative embodiment AE, wherein the adhesive is adapted to remain substantially on the at least one peel patch upon removal of the at least one peel patch.

According to alternative embodiment AH, the drape of alternative embodiment T, wherein the first and second fenestrations are adapted to be placed over a patient's subclavian area, and wherein the third and fourth fenestrations are adapted to be placed over the patient's brachial area.

According to alternative embodiment AI, the drape of alternative embodiment AH, wherein the first and second fenestrations are further adapted to be placed over a patient's femoral area via the first and second fenestrations.

According to alternative embodiment AJ, the drape of alternative embodiment T, wherein the drape has a length of between about 115 inches and about 125 inches and a width of between about 75 inches and about 80 inches.

According to alternative embodiment AK, the drape of alternative embodiment T further comprises one or more additional fenestrations.

According to alternative embodiment AL, a medical drape comprises a main portion having a front side, a back side, a first edge, a second edge, a top, and a bottom, the first and second edges being positioned opposite one another, the top and the bottom being positioned opposite one another, a first fenestration and a second fenestration extending completely through the main portion, the first and second fenestrations being spaced generally equidistant from a vertical axis, the vertical axis being generally parallel to the first and second edges, and a third fenestration and a fourth fenestration extending completely through the main portion, the third and fourth fenestrations being spaced generally equidistant from the vertical axis, wherein the first and second fenestrations are closer to the top than the third and fourth fenestrations.

According to alternative embodiment AM, the drape of alternative embodiment AL further comprises a reinforcement portion coupled to the front side of the main portion, wherein the first, second, third, and fourth fenestrations extend completely through the reinforcement portion.

According to alternative embodiment AN, the drape of alternative embodiment AL, wherein the third and fourth fenestrations are positioned a greater distance from the vertical axis than the first and second fenestrations.

According to alternative embodiment AO, the drape of alternative embodiment AL, wherein the third and fourth fenestrations are positioned generally the same distance from the vertical axis as the first and second fenestrations.

According to alternative embodiment AP, a medical drape comprises a main portion having a front side, a back side, a first edge, a second edge, a top, and a bottom, the first and second edge being positioned opposite one another, the top and bottom being positioned opposite one other, a reinforcement portion coupled to the front side of the main portion, a first side portion coupled to a first edge of the main portion, a second side portion coupled to a second edge of the main portion, a first fenestration and a second fenestration extending completely through the main portion and the reinforcement portion, the first and second fenestrations being spaced generally equidistant from a vertical axis, the vertical axis being generally parallel to the first and second edges, a third fenestration and a fourth fenestration extending completely through the main portion and the reinforcement portion, the third and fourth fenestrations being spaced generally equidistant from the vertical axis, and at least one peel patch removably coupled to the front side of the main portion, the at least one peel patch being positioned over at least one of the first, second, third, and fourth fenestrations, wherein the first and second fenestrations are closer to the top than the third and fourth fenestrations.

According to alternative embodiment AQ, the drape of alternative embodiment AP, wherein the third and fourth fenestrations are positioned a greater distance from the vertical axis than the first and second fenestrations.

According to alternative embodiment AR, the drape of alternative embodiment AP, wherein the third and fourth fenestrations are positioned generally the same distance from the vertical axis as the first and second fenestrations.

According to alternative process AS, a method of making a medical drape comprises the acts of providing a main portion having a front side, a back side, a first edge, a second edge, a top, and a bottom, the first and second edges being positioned opposite one another, the top and the bottom being positioned opposite one another, forming a first fenestration extending completely through the main portion, forming a second fenestration extending completely through the main portion, the second fenestration being spaced generally the same distance from a vertical axis and the top as the first fenestration, the vertical axis being generally parallel to the first and second edges, forming a third fenestration extending completely through the main portion, the third fenestration being positioned farther from the top than the first and second fenestrations, and forming a fourth fenestration extending completely through the main portion, the fourth fenestration being spaced generally the same distance from the vertical axis and the top as the third fenestration.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A medical drape comprising:
a plurality of fenestrations extending completely through a main portion of the medical drape, the fenestrations being generally contoured to the shape of an area of the body to which they are adjacent;
a generally transparent peel patch removably positioned over at least one of the plurality of fenestrations, the peel patch including a patient-facing side having an inner portion and an outer portion, the outer portion including adhesive for coupling the outer portion to the main portion of the medical drape, the inner portion having no adhesive;
an incise film positioned over one or more of the plurality of fenestrations, the incise film including an adhesive side facing a patient; and
a release liner overlying all or a portion of at least one of the plurality of fenestrations, the release liner contacting the adhesive side of the incise film.

2. The medical drape of claim 1, wherein the outer portion of the peel patch includes outer edges, the outer edges having adhesive, the peel patch being removably coupled to the main portion via the adhesive outer edges.

3. The medical drape of claim 2, further comprising a slick surface surrounding at least one of the plurality of fenestrations, wherein the outer adhesive edges of the peel patch overlie a corresponding at least one slick surface.

4. The medical drape of claim 2, wherein the adhesive is adapted to remain substantially on the peel patch upon removal of the peel patch from the medical drape.

5. The medical drape of claim 1, further comprising a reinforcement portion coupled to a front side of the main portion, wherein the plurality of fenestrations extend completely through the reinforcement portion.

6. The medical drape of claim 1, wherein the at least one of the plurality of fenestrations generally contoured to the shape of at least one of the subclavian area, the femoral area and the brachial area.

7. The medical drape of claim 1, wherein the plurality of fenestrations includes a first fenestration and a second fenestration that are angled such that the respective tops of the first and second fenestration are closer to a vertical axis than the respective bottoms of the first and second fenestrations.

8. The medical drape of claim 1, wherein at least one of the plurality of fenestrations being generally oval-shaped, pear-shaped or football-shaped.

9. The medical drape of claim 1, wherein at least one of the plurality of fenestrations being generally oval-shaped, pear-shaped or football-shaped and at least one of the plurality of fenestrations being generally rectangular-shaped or square-shaped.

10. A medical drape comprising:
a main portion having a front side, a back side, a first edge, a second edge, a top, and a bottom, the first and second edges being positioned opposite one another, the top and the bottom being positioned opposite one another;
a plurality of fenestrations extending completely through the main portion, the fenestrations being generally contoured to the shape of an area of the body to which they are adjacent; and
a generally transparent peel patch removably positioned over at least one of the plurality of fenestrations, the peel patch including a patient-facing side having an inner portion and an outer portion, the outer portion including adhesive for coupling the outer portion to the main portion of the medical drape, the inner portion having no adhesive.

11. The medical drape of claim 10, wherein at least one of the plurality of fenestrations being generally contoured to the shape of the subclavian area.

12. The medical drape of claim 10, wherein at least one of the plurality of fenestrations being generally contoured to the shape of the femoral area.

13. The medical drape of claim 10, wherein at least one of the plurality of fenestrations being generally contoured to the shape of the brachial area.

14. The medical drape of claim 10, wherein the plurality of fenestrations includes a first fenestration and a second fenestration that are angled such that the respective tops of the first and second fenestration are closer to a vertical axis than the respective bottoms of the first and second fenestrations.

15. The medical drape of claim 10, further comprising a slick surface surrounding at least one of the plurality of fenestrations.

16. The medical drape of claim 10, wherein the adhesive on the outer portion of the peel patch remains substantially on the peel patch after the peel patch has been removed.

17. The medical drape of claim 10, wherein at least one of the plurality of fenestrations being generally oval-shaped, pear-shaped or football-shaped.

18. The medical drape of claim 10, wherein at least one of the plurality of fenestrations being generally oval-shaped, pear-shaped or football-shaped and at least one of the plurality of fenestrations being generally rectangular-shaped or square-shaped.

* * * * *